US005620970A

United States Patent [19]
Han et al.

[11] Patent Number: 5,620,970
[45] Date of Patent: Apr. 15, 1997

[54] TOPICAL OPHTHALMIC CARBONIC ANHYDRASE INHIBITOR FORMULATIONS

[75] Inventors: Wesley W. Han, Fort Worth; Thomas R. Dean, Weatherford; Steven H. Gerson, Fort Worth; Yusuf Ali, Fort Worth; Rajni Jani, Fort Worth, all of Tex.

[73] Assignee: Alcon Laboratories, Inc., Fort Worth, Tex.

[21] Appl. No.: 461,329

[22] Filed: Jun. 5, 1995

[51] Int. Cl.$^6$ .............. A61J 1/05; A61K 9/08; A61K 31/355; A61K 47/34

[52] U.S. Cl. ........ 514/211; 514/212; 514/222.8; 514/224.2; 514/226.5; 514/232.5; 514/233.8; 514/253; 514/316; 514/318; 514/321; 514/338; 514/373; 514/422; 514/432; 514/762; 514/912; 514/913; 514/914

[58] Field of Search .................. 514/211, 212, 514/222.8, 224.2, 226.5, 232.5, 233.8, 253, 316, 318, 321, 338, 373, 432, 422, 762, 912, 913, 914

[56] References Cited

U.S. PATENT DOCUMENTS

| | | | |
|---|---|---|---|
| 4,797,413 | 1/1989 | Baldwin et al. | 514/432 |
| 4,829,088 | 5/1989 | Doulakas | 514/567 |
| 4,960,799 | 10/1990 | Nagy | 514/567 |
| 5,147,647 | 9/1992 | Darougar | 424/427 |
| 5,153,192 | 10/1992 | Dean et al. | 514/226.5 |
| 5,240,923 | 8/1993 | Dean et al. | 514/226.5 |
| 5,378,703 | 1/1995 | Dean et al. | 514/222.8 |

OTHER PUBLICATIONS

Hata, Murano, and Ueda, CA 118:261059, Ophthalmic Solutions Containing Cyclosporin and Surfactants (1993).
Koide, CA 122:17250, Vitamin A–Solubilized Eye Drops (1995).
Fukahori, Uchino, and Takahashi, CA 118:109767, Aqueous Vitamin E Solutions Containing Surfactants (1993).
Fukahori, Takahashi, and Uchino, CA 114:254038, Stable Eye Drops Containing Vitamin E, FAD Sodium Salt, Allantoin, and Glycyrrhizin (1991).
Takahashi, Fukahori, Uchino, and Eino, CA 114:254039, Stable FAD Sodium Salt or Cyanocobalamine Eye Drops (1991).
Koide and Kojima, CA 120:86468, Stable Eyedrops of Naphazoline Containing Nonionic Surfactants and Glycyrrhizinate Salts (1994).
Koide, CA121:91816, Stable Solutions Containing Solubilized Vitamin A Derivatives (1994).
Koide and Aoshima, CA 121:308384, Stable Vitamin A–and E–Solubilized Eye Drops (1994).

*Primary Examiner*—Nathan M. Nutter
*Attorney, Agent, or Firm*—Sally Yeager

[57] ABSTRACT

The present invention is directed to topical ophthalmic formulations of carbonic anhydrase inhibitors and polyethoxylated derivatives of castor oil. Methods for using the formulations for treating and controlling glaucoma and ocular hypertension are also disclosed.

12 Claims, No Drawings

TOPICAL OPHTHALMIC CARBONIC ANHYDRASE INHIBITOR FORMULATIONS

The present invention is directed to topical ophthalmic formulations useful for treating and controlling glaucoma and ocular hypertension.

BACKGROUND OF THE INVENTION

The use of certain polyethoxylated ether derivatives of castor oil as surfactants and/or emulsifiers in topical ophthalmic formulations is known. See Hata, Murano, and Ueda, CA 118:261059, *Ophthalmic solutions containing cyclosporin and surfactants;* Koide, CA 122:17250, *Vitamin A-solubilized eye drops;* Fukahori, Uchino, and Takahashi, CA 118:109767, *Aqueous vitamin E solutions containing surfactants;* Fukahori, Takahashi, and Uchino, CA 114:254038, *Stable eye drops containing vitamin E, FAD sodium salt, allantoin, and glycyrrhizin;* Takahashi, Fukahori, Uchino, and Eino, CA 114:254039, *Stable FAD sodium salt or cyanocobalamine eye drops;* Koide and Kojima, CA 120:86468, *Stable eyedrops of naphazoline containing non-ionic surfactants and glycyrrhizinate salts;* Koide, CA 121:91816, *Stable solutions containing solubilized vitamin A derivatives;* Nagy, U.S. Pat. No. 4,960,799, *Stabilized Aqueous Solutions of Pharmaceutically Acceptable Salts of Ortho-(2,6-Dichlorophenyl)-Amino-Phenylacetic Acid for Ophthalmic Use,* Oct. 2, 1990 and related Product Insert for Voltaren Ophthalmic; Doulakas, U.S. Pat. No. 4,829,088, *Medicament for the Treatment of Inflammations of the Eye,* May 9, 1989; and Koide and Aoshima, CA 121:308384, *Stable Vitamin A- and E-solubilized eye drops.*

The use of carbonic anhydrase inhibitors (CAIs) in topical ophthalmic formulations for lowering intraocular pressure is known. See, for example, U.S. Pat. Nos. 5,153,192; 5,240,923; 5,378,703; and 4,797,413. Although CAIs are very useful in lowering intraocular pressure, they are typically difficult to formulate at physiological pH due to their sparing solubility except at uncomfortably low pHs. Formulation has also proved challenging due to the instability of some CAIs.

The compositions of the present invention overcome the problems associated with prior CAI compositions in that they are comfortable and stable.

SUMMARY OF THE INVENTION

The compositions of the present invention contain a CAI, and a polyethoxylated ether derivative of castor oil. The invention also includes methods for treating and controlling glaucoma and ocular hypertension by administering the compositions topically to an affected mammalian eye.

DETAILED DESCRIPTION OF THE PREFERRED EMBODIMENTS

The compositions of this invention contain a CAI and a polyethoxylated derivative of castor oil. The compositions are efficacious in treating and controlling glaucoma and ocular hypertension. In addition, the compositions are surprisingly comfortable and stable and the efficacy of the composition's preservative is maintained.

The compositions contain a CAI, such as those disclosed in U.S. Pat. Nos. 5,153,192; 5,240,923; 5,378,703; and 4,797,413, the contents of which are incorporated by reference.

The compositions also contain a polyethoxylated derivative of castor oil. These derivatives are formed by the ethoxylation of castor oil with ethylene oxide. Castor oil is generally composed of about 87% ricinoleic acid, 7% oleic acid, 3% linoleic acid, 2% palmitic acid, and 1% stearic acid. The reaction of varying molar ratios of ethylene oxide with castor oil yields different polyethoxylated castor oil derivatives. The derivatives of the present invention include products resulting from the reaction of from 2–200 moles of ethylene oxide per one mole of castor oil. The derivatives can also be hydrogenated. The most preferred derivative is known as Polyoxyl 35 Castor Oil, also known as Cremophor EL (available from BASF Corp., Parsippany, N.J.).

The compositions can also include ophthalmologically acceptable preservatives, viscosity enhancers, penetration enhancers, buffers, sodium chloride, mannitol, and water to form aqueous, sterile ophthalmic suspensions or solutions. Furthermore, the compositions may contain a thickener such as cellulosics (e.g. hydroxymethylcellulose, hydroxyethylcellulose, hydroxypropylmethylcellulose, methylcellulose), polyvinylpyrrolidone, carbomers or the like to improve the retention of the medicament in the conjunctival sac.

The CAI compositions of the present invention are preferably formulated as topical ophthalmic suspensions or solutions, with a pH of about 4.0–8.0, preferably 4.0–6.0 for solutions and 6.0–8.0 for suspensions. The CAIs will normally be contained in these formulations at concentrations of 0.1–10 weight/volume percent (wt/v %), but preferably about 0.25–5.0 wt/v %. The polyethoxylated ether derivative of castor oil is present at concentrations between 0.01–10.0 wt/v %, preferably 0.5–3.0 wt/v %. The formulations will also preferably contain a preservative, such as, benzalkonium chloride, at concentrations from 0.001–0.1 wt/v %.

Thus, for topical treatment of glaucoma and ocular hypertension, one to three drops of these formulations would be delivered to the surface of the eye one to four times a day according to the routine discretion of a skilled clinician.

The preferred composition is set forth in Example 3. All compositions can be formulated according to the routine discretion of one skilled in the ophthalmic formulations art.

EXAMPLE 1

(R)-(+)-6-(Aminosulfonyl)-4-ethylamino-3,4-dihydro-2H-thieno[3,2-e]-1, 2-thiazine-2-butanoic acid 1, 1-dioxide (1-methyl)ethyl ester hydrochloride (CAI)

| Ingredient | Concentration (wt./v %) |
| --- | --- |
| CAI | 1.08% |
| Cremophor EL | 1.5% |
| Sodium Acetate (Trihydrate) | 0.1% |
| Mannitol | 4.1% |
| Disodium EDTA (Edetate Disodium) | 0.01% |
| Benzalkonium Chloride Solution | 0.01% |
| Hydroxypropyl Methylcellulose (2910) (E4M) | 0.8% |
| Hydrochloric Acid/Sodium Hydroxide | pH 5.0 |
| Purified Water | qs 100% |

EXAMPLE 2

(R)-(+)-6-(Aminosulfonyl)-4-ethylamino-3, 4-dihydro-2H-thieno[3,2-e]-1, 2-thiazine-2-butanoic acid 1, 1-dioxide ethyl ester hydrochloride (CAI)

| Ingredient | Concentration (wt./v %) |
|---|---|
| CAI | 1.08% |
| Cremophor EL | 1.5% |
| Sodium Acetate (Trihydrate) | 0.1% |
| Mannitol | 4.1% |
| Disodium EDTA (Edetate Disodium) | 0.01% |
| Benzalkonium Chloride Solution | 0.01% |
| Hydroxypropyl Methylcellulose (2910) (E4M) | 0.8% |
| Hydrochloric Acid/Sodium Hydroxide | pH 5.0 |
| Purified Water | qs 100% |

EXAMPLE 3

(R)-(+)-6-(Aminosulfonyl)-4-ethylamino-3, 4-dihydro-2H-thieno[3,2-e]-1, 2-thiazine-2-butanoic acid 1, 1-dioxide ethyl ester hydrochloride (CAI)

| Ingredient | Concentration (wt./v %) |
|---|---|
| CAI | 1.08% |
| Cremophor EL | 1% |
| Sodium Acetate (Trihydrate) | 0.1% |
| Mannitol | 4.1% |
| Disodium EDTA (Edetate Disodium) | 0.01% |
| Benzalkonium Chloride Solution | 0.01% |
| Hydroxypropyl Methylcellulose (2910) (E4M) | 0.8% |
| Hydrochloric Acid/Sodium Hydroxide | pH 5.0 |
| Purified Water | qs 100% |

EXAMPLE 4

(R)-(+)-6-(Aminosulfonyl)-4-ethylamino-3, 4-dihydro-2H-thieno[3,2-e]-1, 2-thiazine-2-butanoic acid 1, 1-dioxide ethyl ester hydrochloride (CAI)

| Ingredient | Concentration (wt./v %) |
|---|---|
| CAI | 1.08% |
| Cremophor EL | 0.5% |
| Sodium Acetate (Trihydrate) | 0.1% |
| Mannitol | 4.1% |
| Disodium EDTA (Edetate Disodium) | 0.01% |
| Benzalkonium Chloride Solution | 0.01% |
| Hydroxypropyl Methylcellulose (2910) (E4M) | 0.8% |
| Hydrochloric Acid/Sodium Hydroxide | pH 5.0 |
| Purified Water | qs 100% |

EXAMPLE 5

(R)-(+)-6-(Aminosulfonyl)-4-ethylamino-3, 4-dihydro-2H-thieno[3,2-e]-1, 2-thiazine-2-butanoic acid 1, 1-dioxide ethyl ester hydrochloride (CAI)

| Ingredient | Concentration (wt./v %) |
|---|---|
| CAI | 1.08% |
| Cremophor EL | 0.25% |
| Sodium Acetate (Trihydrate) | 0.1% |
| Mannitol | 4.1% |
| Disodium EDTA (Edetate Disodium) | 0.01% |
| Benzalkonium Chloride Solution | 0.01% |
| Hydroxypropyl Methylcellulose (2910) (E4M) | 0.8% |
| Hydrochloric Acid/Sodium Hydroxide | pH 5.0 |
| Purified Water | qs 100% |

EXAMPLE 6

(R)-(+)-6-(Aminosulfonyl)-4-ethylamino-3, 4-dihydro-2H-thieno[3,2-e]-1, 2-thiazine-2-butanoic acid 1, 1-dioxide ethyl ester hydrochloride (CAI)

| Ingredient | Concentration (wt./v %) |
|---|---|
| CAI | 0.324% |
| Cremophor EL | 1.5% |
| Sodium Acetate (Trihydrate) | 0.1% |
| Mannitol | 4.1% |
| Disodium EDTA (Edetate Disodium) | 0.01% |
| Benzalkonium Chloride Solution | 0.01% |
| Hydroxypropyl Methylcellulose (2910) (E4M) | 0.8% |
| Hydrochloric Acid/Sodium Hydroxide | pH 5.0 |
| Purified Water | qs 100% |

EXAMPLE 7

(S,S)-(−)-4-Ethylamino-5, 6-dihydro-6-methyl-4H-thieno[2,3-b]thiopyran-2-sulfonamide 7, 7-dioxide hydrochloride (CAI)

| Ingredient | Concentration (wt./v %) |
|---|---|
| CAI | 1.12% |
| Cremophor EL | 1.5% |
| Dibasic Sodium Phosphate (Anhydrous), USP | 0.1% |
| Monobasic Sodium Phosphate (Monohydrate), USP | 0.02% |
| Mannitol | 4.1% |
| Disodium EDTA (Edetate Disodium) | 0.01% |
| Benzalkonium Chloride Solution | 0.01% |
| Hydroxypropyl Methylcellulose (2910) (E4M) | 0.8% |
| Hydrochloric Acid/Sodium Hydroxide | pH 5.0 |
| Purified Water | qs 100% |

EXAMPLE 8

(S,S)-(−)-4-Ethylamino-5, 6-dihydro-6-methyl-4H-thieno[2,3-b]thiopyran-2-sulfonamide 7, 7-dioxide hydrochloride (CAI)

| Ingredient | Concentration (wt./v %) |
| --- | --- |
| CAI | 2.24% |
| Cremophor EL | 1.5% |
| Dibasic Sodium Phosphate (Anhydrous), USP | 0.1% |
| Monobasic Sodium Phosphate (Monohydrate), USP | 0.02% |
| Mannitol | 4.1% |
| Disodium EDTA (Edetate Disodium) | 0.01% |
| Benzalkonium Chloride Solution | 0.01% |
| Hydroxypropyl Methylcellulose (2910) (E4M) | 0.8% |
| Hydrochloric Acid/Sodium Hydroxide | pH 5.0 |
| Purified Water | qs 100% |

EXAMPLE 9

(S,S)-(−)-4-Ethylamino-5, 6-dihydro-6-methyl-4H-thieno[2,3-b]thiopyran-2-sulfonamide 7, 7-dioxide hydrochloride (CAI)

| Ingredient | Concentration (wt./v %) |
| --- | --- |
| CAI | 2.24% |
| Cremophor EL | 1.5% |
| Sodium Acetate (Trihydrate) | 0.1% |
| Mannitol | 4.1% |
| Disodium EDTA (Edetate Disodium) | 0.01% |
| Benzalkonium Chloride Solution | 0.01% |
| Hydroxypropyl Methylcellulose (2910) (E4M) | 0.8% |
| Hydrochloric Acid/Sodium Hydroxide | pH 5.0 |
| Purified Water | qs 100% |

EXAMPLE 10

(S,S)-(−)-4-Ethylamino-5, 6-dihydro-6-methyl-4H-thieno[2,3-b]thiopyran-2-sulfonamide 7, 7-dioxide hydrochloride (CAI)

| Ingredient | Concentration (wt./v %) |
| --- | --- |
| CAI | 1.12% |
| Cremophor EL | 1.5% |
| Sodium Acetate (Trihydrate) | 0.1% |
| Mannitol | 4.1% |
| Disodium EDTA (Edetate Disodium) | 0.01% |
| Benzalkonium Chloride Solution | 0.01% |
| Hydroxypropyl Methylcellulose (2910) (E4M) | 0.8% |
| Hydrochloric Acid/Sodium Hydroxide | pH 5.0 |
| Purified Water | qs 100% |

EXAMPLE 11

4-Ethylamino-3,4-dihydro-2-(3-methoxy)propyl-2H-thieno[3,2-e]-1, 2-thiazine-6-sulfonamide 1, 1-dioxide (CAI)

| Ingredient | Concentration (wt./v %) |
| --- | --- |
| CAI | 0.5% |
| Cremophor EL | 1.0% |
| Dibasic Sodium Phosphate (Anhydrous), USP | 0.2% |
| Mannitol | 4.0% |
| Disodium EDTA (Edetate Disodium) | 0.1% |
| Benzalkonium Chloride Solution | 0.01% |
| Hydroxypropyl Methylcellulose (2910) (E4M) | 0.8% |
| Hydrochloric Acid/Sodium Hydroxide | pH 7.4 |
| Purified Water | qs 100% |

EXAMPLE 12

4-Ethylamino-3,4-dihydro-2-(3-methoxy)propyl-2H-thieno[3,2-e]-1, 2-thiazine-6-sulfonamide 1, 1-dioxide (CAI)

| Ingredient | Concentration (wt./v %) |
| --- | --- |
| CAI | 0.4% |
| Cremophor EL | 3.0% |
| Sodium Acetate (Trihydrate) | 0.1% |
| Mannitol | 4.1% |
| Disodium EDTA (Edetate Disodium) | 0.01% |
| Benzalkonium Chloride Solution | 0.01% |
| Hydroxypropyl Methylcellulose (2910) (E4M) | 0.8% |
| Hydrochloric Acid/Sodium Hydroxide | pH 5.0 |
| Purified Water | qs 100% |

What is claimed is:

1. A topical ophthalmic composition for treating and controlling glaucoma and ocular hypertension comprising 0.1–10.0 wt. % of a carbonic anhydrase inhibitor and 0.01–10.0 wt. % of a polyethoxylated derivative of castor oil resulting from the reaction of from 2–200 moles of ethylene oxide per 1 mole of castor oil, wherein said derivatives can be hydrogenated.

2. The composition of claim 1 wherein the polyethoxylated derivative of castor oil results from the reaction of 35 moles of ethylene oxide with 1 mole of castor oil.

3. The composition of claim 1 wherein the carbonic anhydrase inhibitor is selected from the group consisting of (R)-(+)-6-(Aminosulfonyl)-4-ethylamino-3,4-dihydro-2H-thieno[3,2-e]-1, 2-thiazine-2-butanoic acid 1, 1-dioxide (1-methyl)ethyl ester hydrochloride; (R)-(+)-6-(Aminosulfonyl)-4-ethylamino-3, 4-dihydro-2H-thieno[3,2-e]-1, 2-thiazine-2-butanoic acid 1, 1-dioxide ethyl ester hydrochloride; (S,S)-(−)-4-Ethylamino-5, 6-dihydro-6-methyl-4H-thieno[2,3-b]thiopyran-2-sulfonamide 7, 7-dioxide hydrochloride; and 4-Ethylamino-3,4-dihydro-2-(3-methoxy)propyl-2H-thieno[3,2-e]-1, 2-thiazine-6-sulfonamide 1, 1-dioxide.

4. The composition of claim 1 which further comprises a preservative at a concentration of 0.001–0.1 wt. %.

5. The composition of claim 4 wherein the preservative is benzalkonium chloride.

6. A topical ophthalmic composition for treating and controlling glaucoma and ocular hypertension comprising 0.1–10.0 wt. % of a carbonic anhydrase inhibitor selected from the group consisting of (R)-(+)-6-(Aminosulfonyl)-4-ethylamino-3,4-dihydro-2H-thieno[3,2-e]-1, 2-thiazine-2-butanoic acid 1, 1-dioxide (1-methyl)ethyl ester hydrochloride; (R)-(+)-6-(Aminosulfonyl)-4-ethylamino-3, 4-dihydro-2H-thieno[3,2-e]-1, 2-thiazine-2-butanoic acid 1, 1-dioxide ethyl ester hydrochloride; (S,S)-(−)-4-Ethylamino-5, 6-dihydro-6-methyl-4H-thieno[2,3-b]thiopyran-2-sulfonamide 7, 7-dioxide hydrochloride; and 4-Ethylamino-3,4-dihydro-2-(3-methoxy)propyl-2H-thieno[3,2-e]-1, 2-thiazine-6-sulfonamide 1, 1-dioxide; 0.01–10.0 wt. % of a polyethoxylated derivative of castor oil resulting from the reaction of 35 moles of ethylene oxide with 1 mole of castor oil; and 0.001–0.1 wt. % benzalkonium chloride.

7. A method for treating and controlling glaucoma which comprises administering a pharmaceutically effective amount of a composition of 0.1–10.0 wt. % of a carbonic anhydrase inhibitor and 0.01–10.0 wt. % of a polyethoxylated derivative of castor oil resulting from the reaction of from 2–200 moles of ethylene oxide per 1 mole of castor oil, wherein said derivatives can be hydrogenated to an affected eye.

8. The method of claim 7 wherein the polyethoxylated derivative of castor oil results from the reaction of 35 moles of ethylene oxide with 1 mole of castor oil.

9. The method of claim 7 wherein the carbonic anhydrase inhibitor is selected from the group consisting of (R)-(+)-6-(Aminosulfonyl)-4-ethylamino-3,4-dihydro-2H-thieno[3,2-e]-1, 2-thiazine-2-butanoic acid 1, 1-dioxide (1-methyl)ethyl ester hydrochloride; (R)-(+)-6-(Aminosulfonyl)-4-ethylamino-3, 4-dihydro-2H-thieno[3,2-e]-1, 2-thiazine-2-butanoic acid 1, 1-dioxide ethyl ester hydrochloride; (S,S)-(−)-4-Ethylamino-5, 6-dihydro-6-methyl-4H-thieno[2,3-b]thiopyran-2-sulfonamide 7, 7-dioxide hydrochloride; and 4-Ethylamino-3,4-dihydro-2-(3-methoxy)propyl-2H-thieno[3,2-e]-1, 2-thiazine-6-sulfonamide 1, 1-dioxide.

10. The method of claim 7 wherein the composition further comprises a preservative at a concentration of 0.001–0.1 wt. %.

11. The method of claim 10 wherein the preservative is benzalkonium chloride.

12. A method for treating and controlling glaucoma and ocular hypertension which comprises administering a pharmaceutically effective amount of a composition comprising 0.1–10.0 wt. % of a carbonic anhydrase inhibitor selected from the group consisting of (R)-(+)-6-(Aminosulfonyl)-4-ethylamino-3,4-dihydro-2H-thieno[3,2-e]-1, 2-thiazine-2-butanoic acid 1, 1-dioxide (1-methyl)ethyl ester hydrochloride; (R)-(+)-6-(Aminosulfonyl)-4-ethylamino-3, 4-dihydro-2H-thieno[3,2-e]-1, 2-thiazine-2-butanoic acid 1, 1-dioxide ethyl ester hydrochloride; (S,S)-(−)-4-Ethylamino-5, 6-dihydro-6-methyl-4H-thieno[2,3-b]thiopyran-2-sulfonamide 7, 7-dioxide hydrochloride; and 4-Ethylamino-3,4-dihydro-2-(3-methoxy)propyl-2H-thieno[3,2-e]-1, 2-thiazine-6-sulfonamide 1, 1-dioxide; 0.01–10.0 wt. % of a polyethoxylated derivative of castor oil resulting from the reaction of 35 moles of ethylene oxide with 1 mole of castor oil; and 0.001–0.1 wt. % benzalkonium chloride.

* * * * *